US006920660B2

(12) United States Patent
     Lam

(10) Patent No.:     US 6,920,660 B2
(45) Date of Patent:     Jul. 26, 2005

(54) ELECTRIC TOOTHBRUSH REDUCTION GEARBOX

(75) Inventor: Chun Shun Lam, Kwai Chung (HK)

(73) Assignee: Fast Clean Limited, Kwai Chung (HK)

( * ) Notice: Subject to any disclaimer, the term of this patent is extended or adjusted under 35 U.S.C. 154(b) by 321 days.

(21) Appl. No.: 10/208,831

(22) Filed: Aug. 1, 2002

(65) Prior Publication Data

US 2003/0106175 A1 Jun. 12, 2003

(30) Foreign Application Priority Data

Dec. 11, 2001 (CN) .......................................... 01140364

(51) Int. Cl.[7] .............................................. A46B 13/02
(52) U.S. Cl. ........................................ 15/22.1; 15/28
(58) Field of Search ............................... 15/22.1, 22.2, 15/28

(56) References Cited

U.S. PATENT DOCUMENTS

| 5,077,855 | A | * | 1/1992 | Ambasz ....................... 15/22.1 |
| 5,448,792 | A | * | 9/1995 | Wiedemann et al. ........ 15/22.1 |
| 6,446,294 | B1 | * | 9/2002 | Specht ........................ 15/22.1 |

\* cited by examiner

Primary Examiner—Randall Chin
(74) Attorney, Agent, or Firm—Leydig, Voit & Mayer, Ltd.

(57) ABSTRACT

An electric toothbrush includes a handle, a bristle head and a neck extending from the handle to the bristle head. A drive shaft extends through the neck to the bristle head. A motor is situated within the handle and has a pair of spaced recesses and an output shaft situated between the recesses. A reduction gearbox receives torque from the output shaft of the motor and transmits it to the drive shaft at a reduced speed. The gearbox has a base plate having a pair of projections extending into the recesses of the motor, a cover plate fixed to the base plate and at least one gear set between the base plate and the cover plate to transmitting torque from the motor to the drive shaft.

6 Claims, 4 Drawing Sheets

ELECTRIC TOOTHBRUSH REDUCTION GEARBOX

BACKGROUND OF THE INVENTION

The present invention relates to an electric toothbrush having a reduction gearbox. More particularly, although not exclusively, the invention relates to an electric toothbrush having a motor driving an oscillating bristle head via a drive shaft and a reduction gearbox.

Known electric toothbrushes have a handle within which there is situated a battery or batteries, an electric motor receiving power from the batteries via a switch, and a drive shaft extending through a neck of the toothbrush to an oscillating bristle head. As the motor's output is at relatively high RPM compared to the desired oscillation frequency of the bristle head, it would be desirable to reduce the output speed of the motor to drive the drive shaft at lower speed. Electric toothbrushes having a reduction gearbox have been proposed, however, they are of complex design requiring many parts. They have also been mounted to the handle independently of the motor, thereby requiring special attachment to the housing to counteract the motor's output torque.

OBJECT OF THE INVENTION

It is an object of the present invention to overcome or substantially ameliorate at least one of the above disadvantages and/or more generally to provide an electric toothbrush having a motor and a reduction gearbox fitted directly to the motor to counteract the motor's output torque.

It is a further object of the present invention to provide an improved electric toothbrush having a reduction gearbox.

DISCLOSURE OF THE INVENTION

There is disclosed herein an electric toothbrush comprising:
  a handle,
  a bristle head,
  a neck extending from the handle to the bristle head,
  a drive shaft extending through the neck to the bristle head,
  a motor situated within the handle and having a pair of spaced apart recesses and an output shaft situated between the recesses,
  a reduction gearbox receiving torque from the output shaft of the motor and transmitting it to the drive shaft at a reduced speed, the gearbox comprising a base plate having a pair of projections extending into the recesses of the motor, a cover plate fixed to the base plate and at least one gear set between the base plate and the cover plate and transmitting torque from the motor to the drive shaft.

Preferably a first driving gear is mounted upon the output shaft of the motor.

Preferably the base plate has extending therefrom a pin upon which a first driven gear is rotatably mounted.

Preferably the first driven gear has fixedly associated therewith a second driving gear.

Preferably the cover plate has a pair of bridges by which the cover plate is fixed to the base plate.

Preferably the cover plate has a pin upon which a second driven gear is rotatably mounted.

Preferably the second driven gear has extending therefrom an output member received by an end of the drive shaft.

Preferably the output member passes through a retaining plate that is affixed to the cover plate.

BRIEF DESCRIPTION OF THE DRAWINGS

A preferred form of the present invention will now be described by way of example with reference to the accompanying drawings, wherein.

DETAILED DESCRIPTION OF THE PREFERRED EMBODIMENT

Figure 1:
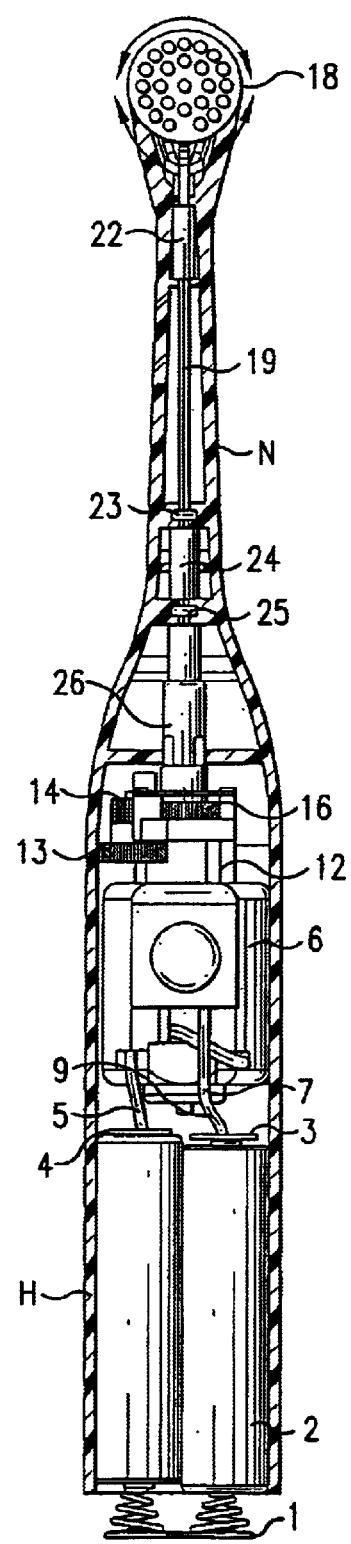
FIG. 1 is a schematic cross-sectional elevational view of a toothbrush.
Figure 2:
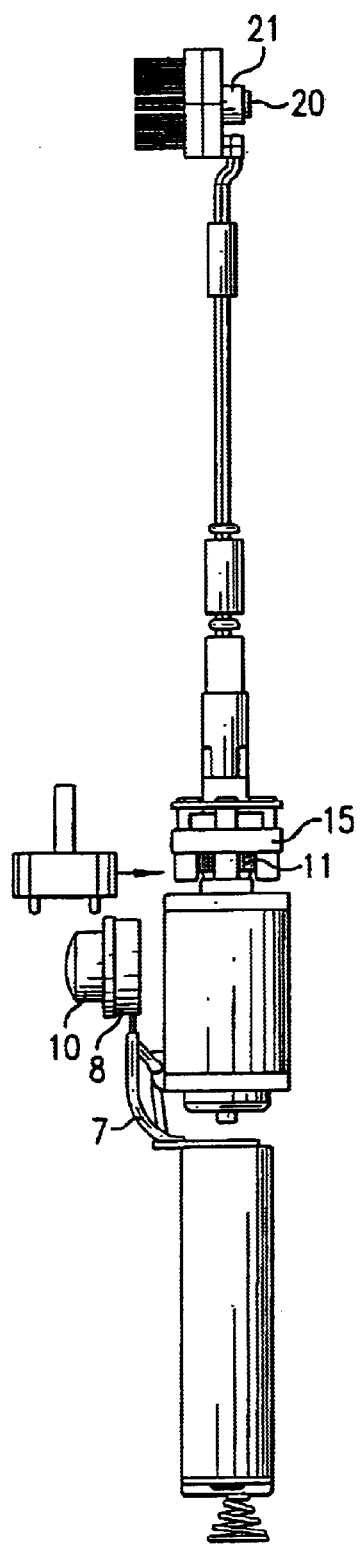
FIG. 2 is a schematic side elevation will view of internal parts of the toothbrush of FIG. 1.
Figure 3:
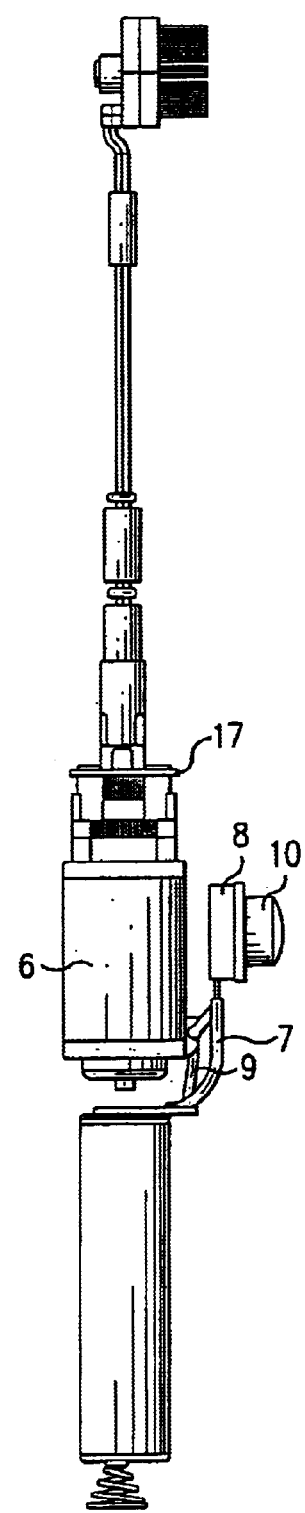
FIG. 3 is a schematic other-side elevational view of the internal parts of the toothbrush of FIG. 2.
Figure 4:
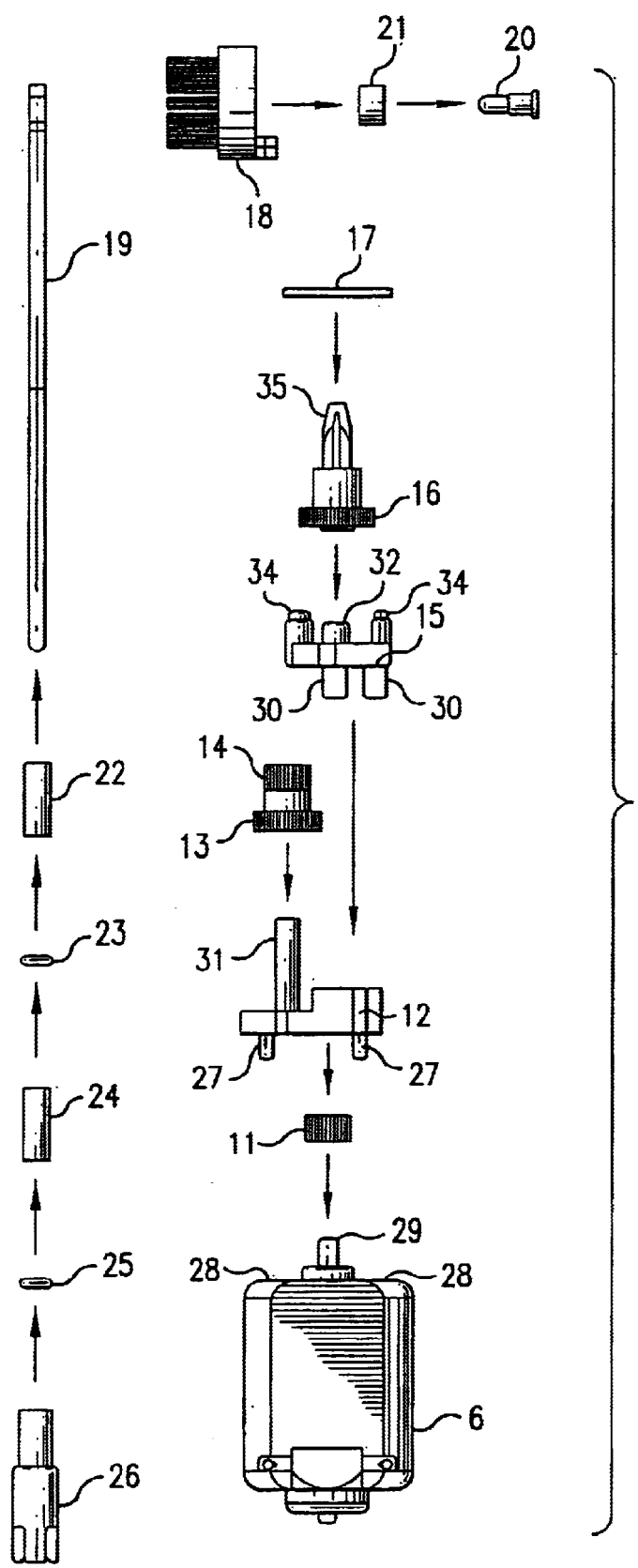
FIG. 4 is a schematic parts-exploded elevational view of drive train components of the toothbrush of FIG. 1, and FIGS. 5A to 5G are schematic illustrations of component parts of the drive train.
Figure 5A:
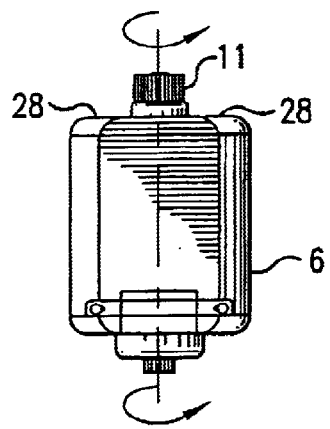
Figure 5B:
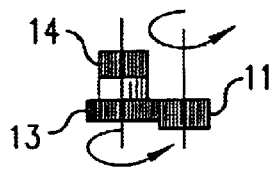
Figure 5C:
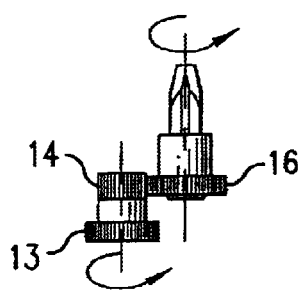
Figure 5D:
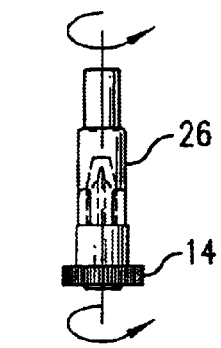
Figure 5E:
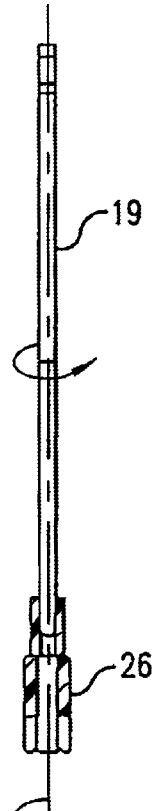
Figure 5F:
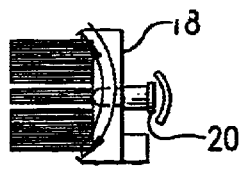
Figure 5G:
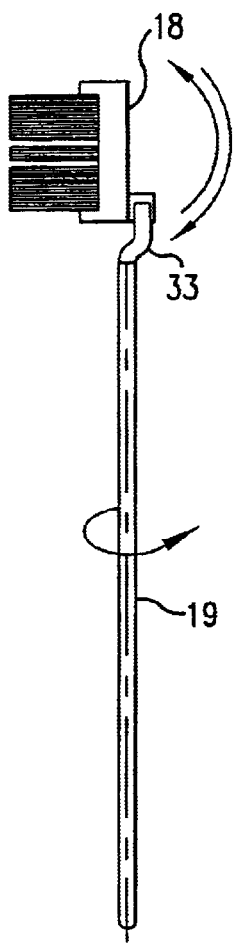

In the accompanying drawings there is schematically depicted an electric toothbrush having a plastics-moulded housing that comprises a handle H and a neck N formed integrally with the handle. Within the handle there is situated a pair of batteries 2. These batteries might be of the disposable or rechargeable type. As an alternative, a single battery might be provided. In the depicted embodiment, there are two batteries connecting series at the base by a coil spring and conductive plate arrangement 1. At the upper end of the batteries, one is connected at 3 to a positive terminal whereas the other is connected 4 to a negative terminal. Positive terminal 3 is connected via a switch wire 7 to a switch 8 that has an ON/OFF button 10. The switch 8 is connected to an electric motor 6 via a switch-motor wire 9. The positive terminal 4 is connected directly to the motor 6 via a battery-motor wire 5. The motor has in its upper surface a pair of recesses 28, between which there is situated an output shaft 29. Mounted directly to the motor 6 is a gearbox base plate 12. Base plate 12 is typically formed of moulded plastic material and has a pair of projections 27 that extended downwardly and into the respective recesses 28. Fixed to the output shaft 29 is a first driving gear 11. The base plate 12 has an outstanding pin 31 onto which a first driven gear 13 is rotatably mounted. The first driven gear 13 meshes with the first driving gear 11. Formed integrally with the first driven gear 13 is a second driving gear 14.

A gearbox cover plate 15 is fixed to the base plate 12 by a pair of bridges 30. That is, the first driving gear 11 and the first driven gear 13 are sandwiched between the base plate 12 and the cover plate 15. This maintains a meshing inter-engagement between the gears 11 and 13.

The cover plate 15 includes a pin 32 upon which there is rotatably mounted a second driven gear 16. This gear is maintained in position upon the pin 32 by a retaining plate 17, typically formed of stainless steel. The plates 12 and 15 are typically formed of moulded plastic materials such as nylon for example. The gears 11, 13, 14 and 16 are typically formed of metal or hard-wearing plastics material such as nylon.

A pair of fixing lugs 34 secures the retaining plate 17 to the cover plate 15. The fixing lugs are formed integrally with the cover plate. These include narrowed top portions that pass through corresponding apertures in the retaining plate and are typically moulded or plastics-welded thereover.

The retaining plate 17 maintains inter-engagement between the second driving gear 14 and the second driven gear 16.

Formed integrally with the second driven gear 16 is an output member 35. Output member 35 might be in the form of an externally tapered or straight spline or a short shaft with a key-way. The output member 35 is received within a coupling 26 that is affixed at an input end of a drive shaft 19 that extends through the neck N of the toothbrush. The drive shaft 19 is mounted in bushings 22 and 24. These bushings maintain the drive shaft 19 within the neck N. A pair of O-ring seals 23 and 25 are also positioned around the drive shaft. These prevent the ingress of liquid downwardly along the shaft toward the gearbox and motor in use. The driveshaft 19 has a dogleg portion 33 that is received within a slot of the bristle head 18. Bristle head 18 is mounted upon a positioning shaft 20 having a positioning sleeve 21. The positioning shaft 20 defines an axis of rotation of the bristle head.

In use, the ON/OFF button 10 is depressed to provide electric current to the motor 6 so as to turn the first driving gear 11. The rotational speed of the motor's output shaft 19 is reduced through the gearbox such that the output member 35 turns at a lower speed. This results in reduced speed and increased torque delivered to the drive shaft 19.

What is claimed is:

1. An electric toothbrush comprising:

a handle, a bristle head, a neck extending from the handle to the bristle head, a drive shaft extending through the neck to the bristle head, a motor situated within the handle and having a pair of spaced apart recesses and an output shaft situated between the recesses, a reduction gearbox receiving torque from the output shaft of the motor and transmitting it to the drive shaft at a reduced speed, the gearbox comprising a base plate having a pair of projections extending into the recesses of the motor, the base plate also having extending therefrom a pin upon which a first driven gear is rotatably mounted, a cover plate fixed to the base plate and at least one gear set between the base plate and the cover plate and transmitting torque from the motor to the drive shaft, wherein the cover plate has a pair of bridges by which the cover plate is fixed to the base plate.

2. The toothbrush of claim 1, wherein a first driving gear is mounted upon the output shaft of the motor.

3. The toothbrush of claim 1, wherein the first driven gear has fixedly associated therewith a second driving gear.

4. The toothbrush of claim 1, wherein the cover plate has a pin upon which a second driven gear is rotatably mounted.

5. The toothbrush of claim 4, wherein the second driven gear has extending therefrom an output member received by an end of the drive shaft.

6. The toothbrush of claim 5, wherein the output member passes through a retaining plate that is affixed to the cover plate.

* * * * *